United States Patent [19]
Kremer

[11] Patent Number: 4,635,488
[45] Date of Patent: Jan. 13, 1987

[54] NONINTRUSIVE BODY FLUID SAMPLERS AND METHODS OF USING SAME
[75] Inventor: Richard D. Kremer, Keene, N.H.
[73] Assignee: Schleicher & Schuell, Inc., Keene, N.H.
[21] Appl. No.: 677,226
[22] Filed: Dec. 3, 1984
[51] Int. Cl.$^4$ ............................................. G01N 1/12
[52] U.S. Cl. ................... 73/864.72; 128/760; 128/771; 422/58; 422/59
[58] Field of Search ............ 73/864.72, 863, 61.1 C; 128/760, 771; 604/1, 312, 318, 364, 358, 365, 366, 367, 370, 374, 375; 422/56, 58, 59, 61, 69, 70; 436/165, 169, 174, 179, 180; 116/206

[56] References Cited
U.S. PATENT DOCUMENTS

| | | |
|---|---|---|
| 2,733,135 | 1/1956 | Huckaby ............................ 422/59 X |
| 3,359,180 | 12/1967 | Evans et al. ...................... 422/56 X |
| 3,368,549 | 2/1968 | Barr et al. ......................... 128/759 |
| 3,388,975 | 6/1968 | Wallace ............................... 422/59 |
| 3,446,596 | 5/1969 | Salivar et al. ................... 422/58 X |
| 3,890,954 | 6/1975 | Greenspan ....................... 604/1 X |
| 4,138,474 | 2/1979 | Updike ............................ 422/58 X |
| 4,190,060 | 2/1980 | Greenleaf et al. ........... 73/864.72 X |
| 4,334,879 | 6/1982 | Fujimori ......................... 436/174 |
| 4,355,113 | 10/1982 | Mennen ......................... 422/61 X |
| 4,425,438 | 1/1984 | Baumon et al. ................. 422/59 X |
| 4,553,966 | 11/1985 | Korteweg ...................... 128/760 X |

FOREIGN PATENT DOCUMENTS

| | | | |
|---|---|---|---|
| 548420 | 12/1924 | France ................................ 604/1 |
| 2331023 | 6/1977 | France ......................... 73/61.1 C |
| 4600 | 2/1972 | Japan ........................... 73/61.1 C |

Primary Examiner—Michael J. Tokar
Assistant Examiner—Tom Noland
Attorney, Agent, or Firm—Cooper, Dunham, Griffin & Moran

[57] ABSTRACT

A body fluid sampling device including a hollow tube with a solid, porous, water-wettable nonfibrous nib mounted in and protruding from one end of the tube for collecting, by absorption, a sample of a body fluid such as sweat, tears, or saliva. The sample may be extracted from the nib for analysis by supplying an extraction fluid to the interior of the tube for gravity or vacuum-assisted flow out through the nib. Alternatively, an elongated analysis element such as a strip of paper or a packed column, e.g. containing an agent that changes appearance to indicate the presence of a substance to be detected, may be disposed in the tube for endwise contact with the nib to receive the sample (or components thereof) by absorption.

23 Claims, 16 Drawing Figures

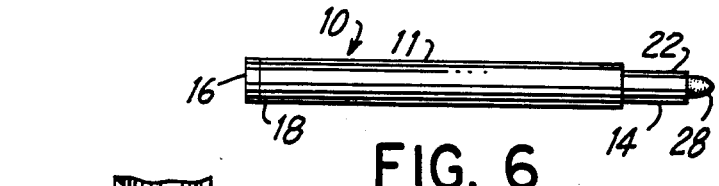
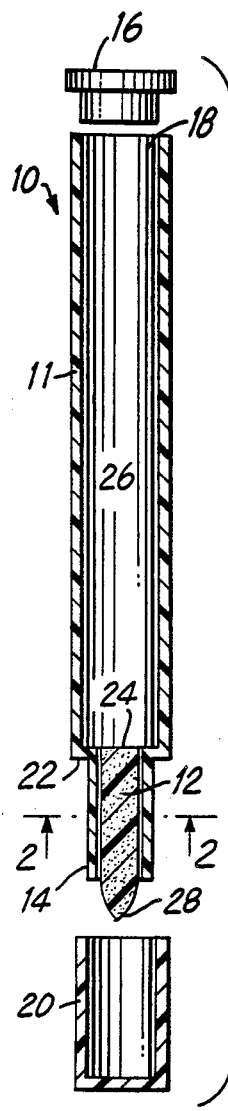
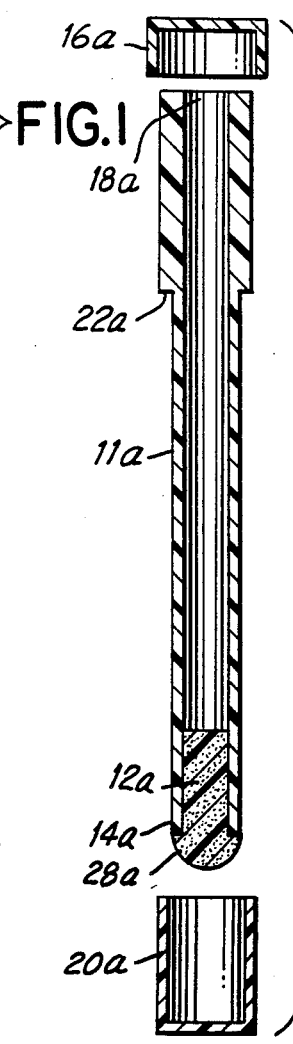
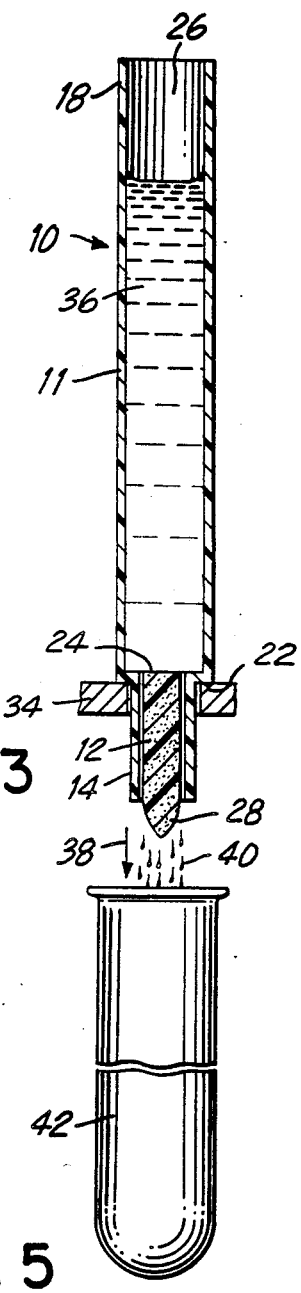
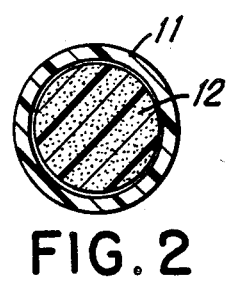

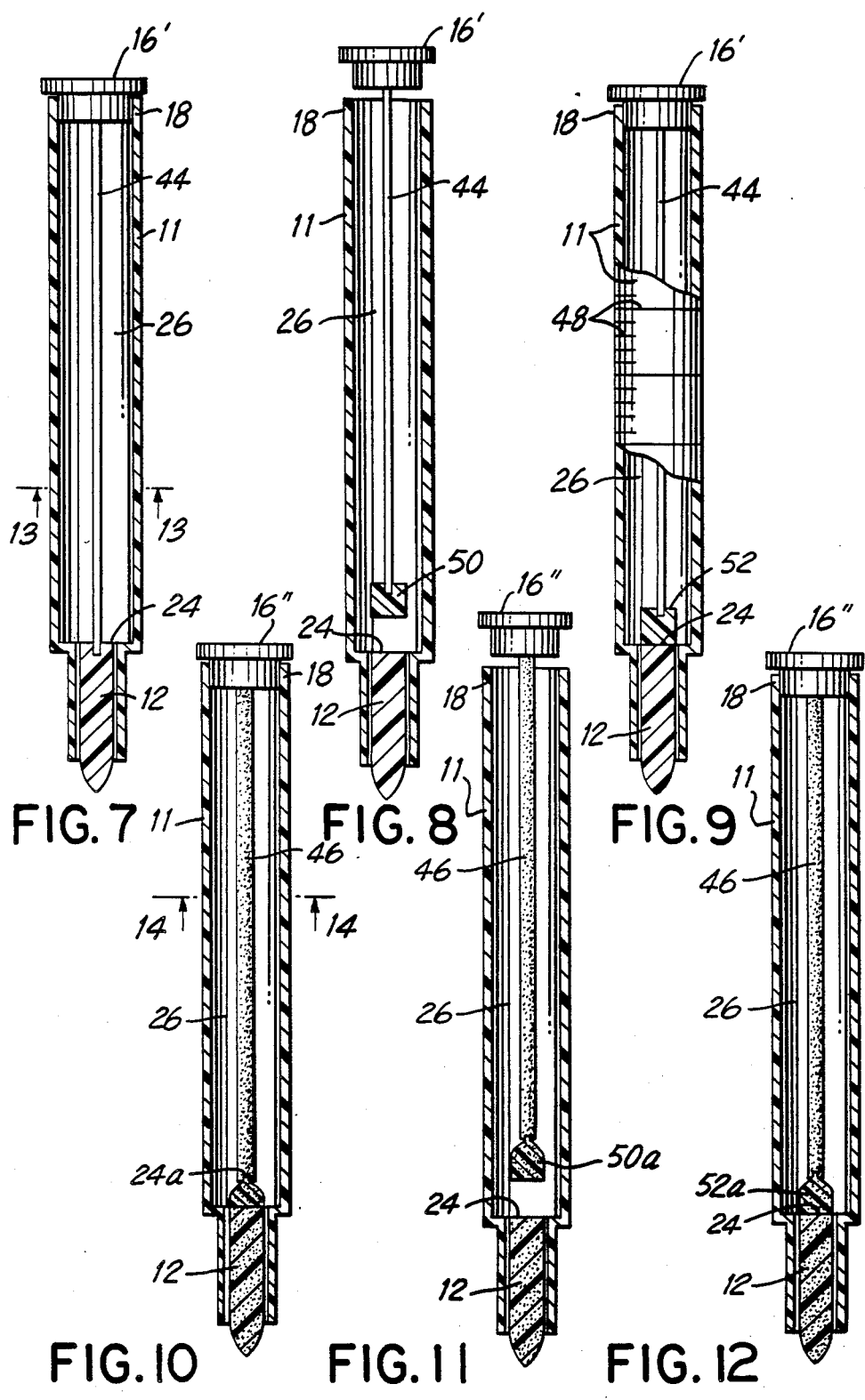

NONINTRUSIVE BODY FLUID SAMPLERS AND METHODS OF USING SAME

BACKGROUND OF THE INVENTION

This invention relates to sampling devices for obtaining samples of body fluids such as sweat, tears and saliva for subsequent analysis, and to methods of using these devices in preparing samples for analysis.

There has been a growing interest in recent years in the nonintrusive clinical sampling of body fluids for detecting various chemical substances. This is largely the result of improved analytical techniques and the realization that many of the components of physiological interest (metabolites, drugs, etc.) contained in blood samples obtained by intrusive means (e.g. venipuncture or finger and heel sticks) are also contained in other body fluids such as sweat, tears and saliva, which can be obtained much more easily and at reduced risk. In addition, these samples may be advantageous for testing for components of physiological interest.

This latter advantage may be illustrated by comparing the utility of urine and saliva samples to establish recent marijuana usage. Since marijuana can be detected in urine for up to 40 days after the last use of the drug, while saliva will only show evidence of such usage within the last 48 hours, saliva samples are much more useful than urine samples for detecting recent use of the drug.

Body fluid sampling and testing usually involves four steps, viz.:
1. sample collection,
2. extraction of the sample from the collection media,
3. reaction of the sample with analytical reagents, and
4. detection and/or measurement of physiologically active contents.

In the past, the nonintrusive collection of body fluid samples has commonly been accomplished by the use of devices such as cotton swabs, absorbent papers and pads, which are used to absorb fluid samples. Once collected, these devices are placed in a vessel in which the sample is extracted into a suitable solvent by means of diffusion, with or without mechanical agitation. Sample extraction by means of unassisted diffusion is quite slow, usually requiring several minutes. If this process is speeded up with agitation, extraneous material such as cotton or paper fibers may be entrained in the extraction fluid along with the sample and may have to be removed prior to the reagent reaction of step 3 above.

Various prior patents disclose different types of samplers and techniques for obtaining and preparing samples for spectral or spot analyses. For example, U.S. Pat. No. 3,452,601 and No. 3,511,570 to Mogayzel et al. disclose the arrangement and use of a device, for obtaining a liquid sample for subsequent spectroscopic analysis, which comprises an elongated porous mass enclosed at least partially by a non-porous tubular member or shield. The sample is obtained by bringing one end of the mass into contact with a solute containing the material to be analyzed. The porous mass acts as a wick and picks up the solute through capillary action. Part of the porous mass containing the sample is removed, crushed, dried and analyzed. In a modification described in U.S. Pat. No. 3,496,777 to Packer et al., a device for preparing samples for spectroscopic analysis is formed of an elongated porous wick enclosed on its sides to prevent evaporation but open at the ends, with a separate porous pointed tip of porous, spectroscopic-grade matrix material removably placed against one end of the wick. The sample, absorbed through the other end of the wick, collects in the tip, which is then removed and crushed for analysis.

U.S. Pat. No. 3,326,205 to Lewis discloses an implement for removing a liquid with a tube while preventing other (particulate) matter from being drawn into the tube. In this device, the tube through which the liquid is removed terminates in a hollow spoon-like collecting member having two co-extensive, connected walls, one wall being smooth and imperforate while the other is perforated or in the form of a mesh or screen.

U.S. Pat. No. 4,334,879 to Fujimori discloses an applicator comprising a holder and an applicator blade of porous, absorbent material formed as a rectangular plate and mounted at the end of the holder. The blade is dipped into a liquid in order to absorb a quantity of the liquid, and is then pushed onto an electrically energizable film to express a fine, uniform sample of liquid onto the film.

U.S. Pat. No. 4,190,060 to Greenleaf et al. describes a sweat collection capsule comprising a frame held on the skin, a closure secured to the frame, and an absorbent material removably mounted next to the skin in a cavity formed by the frame and the closure.

U.S. Pat. No. 3,368,549 to Barr et al. relates to a swab-like structure comprising a support and a culture medium-carrying means on an end portion of the support, with a sterile container provided for removably housing the support.

SUMMARY OF THE INVENTION

An object of the present invention is to provide a simply constructed, inexpensive, discardable nonintrusive sampler for body fluids such as sweat, tears or saliva.

Another object is to provide a sampling device of such type in which an absorbent sample collector and an extraction vessel are combined in a single unit.

Still another object is to provide a sampling device of such type easily understood and used by the person from whom the sample is obtained and the person obtaining it, the device having a shape and size similar to a common oral fever thermometer.

A further object is to provide methods of using such sampling devices.

To these and other ends, the present invention broadly contemplates the provision of a sampling device comprising a hollow tube having at least one open end, and a collecting nib secured in that open end of the tube and having an inner extremity facing the interior of the tube and an outer tip projecting beyond the last-mentioned end of the tube for contact with a fluid to be collected. The nib comprises a solid, nonfibrous, porous, water-wettable body having a porosity sufficient for absorption therein of the fluid to be collected. The nib and the end of the tube in which it is mounted are mutually arranged to permit passage of fluid between the exterior and the interior of the tube, at that end of the tube, only through the nib body. Preferably, the tube has a second open end opposed to the first end, and is provided with a first cap for closing the second open end and a further cap for enclosing the first-mentioned open end of the tube and the nib tip projecting therefrom.

Advantageously, the nib is a unitary molded plastic body, being fabricated, for example, of polyethylene or polypropylene. Since the latter materials are themselves hydrophobic (i.e. not water wettable), nibs formed of these materials are treated with a wetting agent such as a conventional surface-active agent having the known property of imparting water-wettability to polyethylene or polypropylene. In currently preferred embodiments, the nib body and the hollow tube are bonded together by ultrasonic welding, or are secured together by press-fitting or heat sealing.

In accordance with one aspect of the invention, a device of the type described is employed in a method of preparing a body fluid sample for analysis comprising the steps of bringing a fluid sample to be collected into contact with the exposed tip of the nib for absorption of the sample into the nib; passing an extraction fluid through the tube interior and thence outwardly through and beyond the nib for conveying the absorbed sample from the nib; and, outwardly of the nib, collecting the extraction fluid containing the conveyed sample. The extraction fluid may pass outwardly through the nib by gravity flow, i.e. with the tube supported in upright position and the nib pointing downwardly while the interior of the tube is filled with the extraction fluid, or alternatively, the flow of extraction fluid through the nib may be assisted by vacuum or suction.

In accordance with a further aspect of the invention, the device may be provided with a cap for closing the second open end of the tube and with an elongated, absorbent, substantially rigid analysis element such as a strip of test paper or other web material, or a packed column of particles. This analysis element has a proximal end mounted in the cap, such that when the cap is in position closing the aforementioned second open end of the tube, the analysis element extends through the tube and its distal end is in fluid-transferring contact with the inner extremity of the nib to receive and absorb fluid collected by the nib. The distal end of the analysis element may be anchored in the nib, or may comprise a body of porous material arranged for contact with the inner extremity of the nib but so constituted, and/or so manipulated, that transfer of the sample from the nib to the analysis element by absorption occurs only after collection of the sample by the nib has been completed.

In the embodiments of the invention just described, the strip or packed column of the analysis element may incorporate an agent that undergoes an observable change (e.g. a visually observable change, such as a change in color, or a change that may be observed with some appropriate detecting instrument) upon contact with a substance to be detected in a body fluid sample. Thus, the device including the analysis element can provide an immediate analytical or diagnostic indication, by observation through the tube wall (which is transparent), upon collection of a sample by the nib and absorption of the collected sample into the analysis element. Additionally or alternatively, the analysis element may be removed from the tube after absorbing the sample, for subsequent analytical operations.

It is also contemplated to provide a packed column of analytical powder or particles, e.g. conventional chromatographic material in particulate form, filling the entire interior of the tube and either in direct contact with the inner extremity of the nib or isolated therefrom by an absorbent but hydrophobic body (to prevent premature transfer of sample to the packed column), again for the purpose of enabling analysis of a sample by observation of the packed columm through the tube wall.

Particularly for the collection of samples of saliva, the device of the invention may be formed with dimensions and configuration generally similar to a conventional oral thermometer.

Further features and advantages of the invention will be apparent from the detailed description hereinbelow set forth, together with the accompanying drawings.

BRIEF DESCRIPTION OF THE DRAWINGS

FIG. 1 is a sectional elevational view of a body fluid sampling device embodying the present invention in a particular form, with end caps shown in exploded relation to the tube end nib;

FIG. 2 is an enlarged sectional view taken as along the line 2—2 of FIG. 1;

FIG. 3 is a sectional elevational view, similar to FIG. 1, of another embodiment of the invetion;

FIG. 4 is a simplified schematic view in illustration of the use of the device of FIG. 1 in collecting a sample of body fluid;

FIG. 5 is a simplified and somewhat schematic view in illustration of a further step in the use of the FIG. 1 device for preparing a body fluid sample for analysis in accordance with the method of the invention;

FIG. 6 is a reduced side view of the device of FIG. 1;

FIG. 7 is a sectional elevational view of a sampling device in accordance with the invention, incorporating an analysis element comprising a paper strip, viewed edgewise;

FIG. 8 is a similar view of another embodiment of the invention also incorporating an analysis element including a paper strip, viewed edgewise;

FIG. 9 is a similar view (but with only the upper and lower portions of the tube broken away) of yet another embodiment of the invention incorporating an analysis element including a paper strip, viewed edgewise;

FIG. 10 is a view similar to FIG. 7 of an embodiment of the invention incorporating an analysis element comprising a packed column;

FIG. 11 is a view similar to FIG. 10 of an additional embodiment of the invention incorporating an analysis element including a packed column;

FIG. 12 is a similar view of yet another embodiment of the invention, also incorporating an analysis element comprising a packed column;

DETAILED DESCRIPTION

Figure 13:
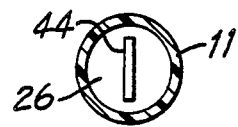
FIG. 13 is a sectional view taken along the line 13—13 of FIG. 7.
Figure 14:
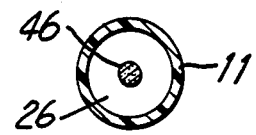
FIG. 14 is a sectional view taken along the line 14—14 of FIG. 10.

Referring first to FIGS. 1 and 2, the body fluid sampler of the invention is there shown as embodied in a device 10 comprising a generally cylindrical, hollow, open-ended tube 11 and a sample-collecting nib 12 mounted in a first open end 14 of the tube 11. A cap 16 is provided for closing the second open end 18 of the tube, and a further cap 20 is provided for externally surrounding and enclosing the nib and the first open end 14 of the tube.

The tube 11 is an integral, rigid, molded element, nonporous and impermeable to fluids, and ordinarily or preferably transparent. It is fabricated of a clinically inert plastic such as (for example) polyethylene or polypropylene. In the embodiment of FIG. 1, the nib-containing portion of the tube adjacent end 14 is of smaller diameter (both internally and externally) than the remainder of the tube so as to provide an annular shoulder or ledge 22 on the outer surface of the tube, facing and spaced from the tube end 14.

The nib 12 is a solid, nonfibrous, but porous, and water-wettable body having a porosity sufficient for absorption therein of a fluid sample to be collected. The flat inner extremity 24 of the nib faces the hollow interior 26 of the tube, while the opposite extremity of the nib is shaped to constitute a tip 28 projecting outwardly beyond the tube end 14 for contact with a fluid to be collected. In the FIG. 1 embodiment, the tip 28 is formed with a generally conical, substantially pointed configuration.

Preferably, the nib is a unitary, integral, molded plastic body, generally cylindrical (except for the pointed end) and dimensioned to conform to the inner diameter of the tube end portion in which it is received. One material suitable for the nib is the porous plastic molded compound commercially available under the registered trademark "POR-X" from Porex Materials Corporation, Fairburn, Ga.; this material is a proprietary composition incorporating a wetting agent so as to be water-wettable, and has been used for the tips of fluid applicators such as marking pens. More generally, the material of the nib 12 may be any moldable plastic which is clinically inert and is capable of being formed into a molded solid yet porous body characterized by a structure of interconnecting pores that can absorb, and transmit by capillary action through its length, a sample of aqueous body fluid. Examples of such materials, satisfactory from the standpoint of cost, availability and ease of fabrication, are polyethylene and polypropylene. Since both of these plastics are hydrophobic in nature, a nib formed thereof is treated with an appropriate wetting agent so as to make it water-wettable, i.e. capable of absorbing aqueous body fluids.

Solid but porous and absorbent molded plastic bodies, appropriate (when provided in proper shape and dimensions) for use as the nib 12, are readily producible by techniques entirely familiar to persons of ordinary skill in the art. The selection of a suitable wetting agent, and the treatment of the porous body therewith to render it hydrophilic or water-wettable, are likewise well known in the art and accordingly need not be further described.

Most of the length of the nib is closely laterally surrounded by the portion of the cylindrical tube wall adjacent tube end 14. For example, the nib 12 and the surrounding portion of the wall of tube 11 can be sealingly bonded together by ultrasonic welding, which joins the inner wall of the tube to the outer side surface of the porous nib along a welded seam extending circumferentially around the nib. Techniques for producing such an ultrasonic weld are, again, well known in the art and accordingly require no showing or description. The ultrasonically welded bond between the nib and tube assures that the nib will remain properly positioned in and projecting from the tube, and that liquid can pass between the interior and the exterior of the tube at the end 14 only through the nib. In other examples of construction of the device, the nib can simply be tightly press-fitted into the end portion of the tube, or can be secured to the tube by heat sealing. Nib-securing arrangements such as these (i.e. ultrasonic welding, press fitting, or heat sealing) afford the advantage of avoiding the use of any material such as an adhesive that might conceivably contaminate the samples being collected.

The end cap 16 is a molded plastic body shaped and dimensioned to be press fitted into the open end 18 of the tube 11 so as to close tightly that end of the tube for protection of the tube interior against contamination. The cap 20 is a molded plastic cup dimensioned to be press fitted over the portion of the tube adjacent the end 14 so as to grip that tube portion, enclosing the exposed nib tip 28, for protection of the nib tip against contamination prior to and/or after use of the device to collect a body fluid sample. Conveniently, all four elements of the device of FIGS. 1 and 2 may be fabricated of the same plastic, e.g. polyethylene or polypropylene.

FIG. 3 illustrates a second embodiment of the sampling device of the invention, differing from that of FIGS. 1 and 2 chiefly in details of configuration. In the FIG. 3 device, the tube 11a, like the tube 11 of FIG. 1, is a generally cylindrical, rigid hollow and open-ended element molded of plastic, with a solid, porous, nonfibrous water-wettable nib 12a received in and projecting beyond one end 14a of the tube. The nib 12a may be essentially identical to the nib 12 of FIG. 1 but is shown as having a projecting tip 28a of substantially rounded (rather than pointed) configuration. The upper portion of the wall of tube 11a is externally thickened to provide an annular shoulder or ledge 22a, again facing and spaced from the nib-containing end 14a of the tube. Cap 16a fits over rather than within the upper end 18a of tube 11a, while cap 20a fits over the nib-containing end of the tube in the same manner as cap 20 of FIG. 1. As before, the nib and tube are bonded by ultrasonic welding.

The showing of FIG. 3 is intended merely to illustrate exemplary modifications of structure of the sampling device of the invention. Many other modifications are of course possible. For instance, the caps 16 or 16a and 20 or 20a and the associated portions of the tube 11 or 11a may be formed with mating threads, i.e. the caps may be threaded in or on rather than press-fitted in or over the ends of the tube.

For convenience, in the remainder of the description of the invention, reference will be made to a sampling device in which the tube, nib and caps are in the form represented in FIGS. 1 and 2, but it will be appreciated that the following disclosure is equally applicable to a device having the form shown in FIG. 3, or to a device having any combination of the features respectively illustrated in FIGS. 1 and 3. As may be most clearly apparent from FIG. 6 (illustrating the embodiment of FIGS. 1 and 2), the device when ready for use to collect a sample (i.e. with cap 20 removed) has preferably the general appearance and dimensions of a conventional oral thermometer. This configuration enhances the acceptability of the device to the persons from whom samples are to be collected, and also facilitates sample collection, e.g. of sweat from the axillae or of saliva from the mouth, the device being insertable in the mouth with the exposed nib tip positioned beneath the tongue to collect saliva.

FIGS. 4 and 5 illustrate schematically the practice of a method in accordance with the invention for preparing a body fluid sample for analysis, utilizing the device of FIGS. 1, 2 and 6. In FIG. 4, there is shown a drop 30 of aqueous body fluid to be collected, such as a tear or a bead of sweat, on a surface 32 of the human body. With the cap 20 removed (but, in this instance, preferably with the tube end 18 still closed by cap 16, for protection against contamination), the exposed tip 28 of the porous nib 12 is brought into contact with the fluid drop 30. The nib, being water wettable, absorbs and retains the drop 30 by wicking or capillary action. In at least many cases, it is preferred that this step be repeated (with successive droplets) or continued (by maintaining the exposed nib 12 under the axilla or tongue) until the nib is completely saturated with the body fluid being collected; since a given porous nib has an essentially fixed fluid capacity, saturation assures collection of a sample of predetermined volume, as is particularly desirable for quantitative analysis. Once the nib is saturated, the cap 20 may be replaced on the tube end 14, to prevent contamination or drying, and the device 10 carrying the collected body fluid sample in the nib may be delivered to a laboratory for extraction and analysis of the sample. Of course, the extraction may be performed immediately if the collecting step is performed at a location where facilities for extraction are at hand.

Collection of a sample with the described device is so simple as to be readily performable by an untrained person, such as the person from whom the sample is taken. The device constitutes an effectively universal nonintrusive body fluid sampler, suited to the collection of samples from diverse sites (eye area, mouth, axillae, etc.). In addition, its ready transportability in a sealed, protected manner, before and after use, makes the device practicable to employ in either a clinical, home or remote location.

In the laboratory, the sample-bearing device 10 is uncapped at both ends, and inserted in a hole in a rack 34 (FIG. 5); the ledge 22 provides a bearing surface, engaging the rack for supporting the tube 11 in an upright position, as shown, with the nib pointing downwardly. The interior 26 of the tube 11 is then filled (through the open upper end 18) with a suitable fluid 36 (e.g., a conventional extraction fluid), for example by means of a pipetting syringe. This fluid is forced by gravity through the upper extremity 24 of the nib, into and through the porous nib body and thence outwardly (i.e. downwardly) through and beyond the nib tip, as indicated by arrow 38 and droplets 40, conveying with it the body fluid sample previously absorbed in the nib. Thus, the downward gravity flow of extraction fluid flushes or purges the collected sample from the nib. Alternatively, a vacuum-assisted flow arrangement (not shown) may be used to draw the extraction fluid from the tube interior 26 through and beyond the nib. In either event, the extraction fluid conveys the collected sample from the nib and into a suitable receptacle or collection vessel 42 (which, accordingly, receives a volume of extraction fluid having the collected body fluid sample admixed therein) for subsequent analysis.

The foregoing preparation method may be compared with conventional sample preparation procedures in which a body fluid sample, absorbed in a fibrous swab or like body, is extracted therefrom by quiescent or agitation-assisted diffusion into an extraction fluid or solvent. In the present method, there is no need to wait for passive diffusion to recover the sample in the solvent, because the sample is actively purged from the nib by the directional (one-way) flow of the fluid 36 through the entire nib. Since the nib is a molded plastic body, there is no possibility of entrainment of absorbent-media fibers in the extraction fluid. Moreover, the combination of the absorbent medium (nib) with the extraction vessel (tube) in a unitary structure facilitates and expedites the extraction operation while minimizing equipment requirements, reducing the likelihood of sample contamination, and, in short, enabling the analyst to obtain the maximum amount of absorbed and extracted sample in the least possible time, free from extraneous materials.

A further virtue of the described sampling device is that it is easy and economical to manufacture. The several parts—tube, nib, and caps—are molded by conventional techniques. The nib is inserted in the end 14 of the tube, with the tip 28 protruding for sample collection, and is bonded to the surrounding portion of the tube wall adjacent end 14 by ultrasonic welding. Positioning of the caps on the ends of the nib-tube unit completes the assembly operation and readies the device for sterilization and packaging. In this way, i.e. with inexpensive materials and simple manufacturing procedures, there is provided a disposable sampling device of beneficially low cost, affording the advantages described above.

If desired, the nib 12 may contain (e.g. as a component of the wetting agent) a reagent or dye which changes color upon contact with a substance to be detected in a body fluid, thereby affording colorimetric test capability.

A further aspect of the invention is illustrated in FIGS. 7-14. In this aspect, the invention contemplates the combination, with a device e.g. of the type shown in FIGS. 1, 2 and 6, of an elongated, absorbent, substantially rigid analysis element extending longitudinally through the interior 26 of the tube 11 for endwise fluid-transferring contact with the inner extremity 24 of the nib 12, so that a body fluid sample collected by the nib is transferred into and absorbed by the analysis element. For example, the analysis element may comprise a strip 44 of paper or other web material, as represented schematically (seen edge-on) in FIGS. 7, 8, and 9, and in section in FIG. 13; or it may comprise a packed column 46 of powder or particles enclosed within a thin glass or transparent plastic tube, as shown in FIGS. 10-12 and 14. Another suitable form of packed column, not shown, is a coating or particles or powder affixed to the outside surface of an elongated rigid support. When the analysis element is a strip of web material, it should include rigidifying support elements such as thin rods or supporting backing (omitted, for simplicity of illustration, from FIGS. 7-9 and 13) unless the web material is itself relatively stiff.

The analysis element 44 or 46 may incorporate an agent that undergoes change of appearance (e.g. color) when it comes into contact with a substance to be detected in a body fluid sample. For instance, the web strip 44 may be impregnated with such an agent, or the element may be constructed of a suitable adsorbent material and constitute a conventional chromatographic strip; similarly, the particles or powder of the packed column 46 may comprise or contain such an agent, being arranged to constitute a chromatographic column. Thus, when the sample collected by the nib 12 climbs by absorption into the analysis element (strip or column), visual observation of color change through the transparent side wall of the tube 11 provides an indication of the presence or absence (in the sample) of the substance to be detected. In some instances, quantitative analysis may be performed in the same way, e.g. by observing the extent to which a color change develops along the analysis element; to facilitate such observation, graduations 48 (FIG. 9) may be marked along the tube 11. In other cases, the active material of the analysis element may undergo changes which are detected by observation with instruments rather than by visual observation. Additionally, or alternatively, in certain of the illustrated embodiments (FIGS. 8, 9, 11 and 12), the analysis element may be removed from the tube 11 after receiving the collected sample (or a component thereof), for subjection to subsequent, more sophisticated or complex, analytical procedures or qualitative or quantitative determinations.

Packed columns 46 afford advantages, for some purposes, over a web strip 44, in that a greater diversity of analytical materials can be provided in packed-column form with consequently greater diversity of types of analysis or separation that can be performed.

In each of the embodiments of FIGS. 7-12, the proximal end of the analysis element 44 or 46 is fixedly mounted in a cap 16' or 16" which closes the upper end 18 of the tube 11, and the distal end of the element 44 or 46 is disposed for contact with the inner extremity 24 of the nib 12 when the cap 16' or 16" is in tube-closing position. As shown in FIGS. 7 and 10, the distal end of the web strip 44 or packed column 46 may be directly, fixedly mounted in or secured to the nib inner extremity 24 or 24a in fluid-transferring contact therewith, the cap 16' or 16" being permanently secured in the tube-closing position. This arrangement has the virtue of structural simplicity, and is satisfactory e.g. for some types of chromatographic qualitative analysis. However, assuming that the web 44 or column 46 is water-wettable (as is ordinarily the case), there is nothing to prevent fluid of a sample being collected by the nib from proceeding on up into the analysis element, once the nib has become saturated. Thus, the amount of fluid collected may indeterminately exceed the saturation volume of the nib, a situation which is undesirable for quantitative testing; moreover, it is not possible, in the arrangements of FIGS. 7 and 10, to utilize secondary solvent absorption procedures for delivery of only a selected component or components (of diagnostic interest) from the collected sample to the analytical element.

In the embodiments of FIGS. 8 and 11, the analysis element includes, at its distal end, a solid porous body 50 or 50a secured to and in fluid-transferring contact with the web strip 44 or column 46. This body 50 or 50a is constituted of the same water-wettable material as the nib 12, and is shaped and disposed to engage the nib inner extremity 24 in fluid-transferring contact therewith when the cap 16' or 16" is in tube-closing position, but is nevertheless fully separable from (not bonded to) the nib. In a method according to the invention for using the device of FIGS. 8 or 11, the body 50 or 50a is maintained entirely away from contact with the nib while a body fluid sample is collected by the nib; conveniently, the analysis element is inserted in the tube 11 only after sample collection is complete. The cap 16' or 16" is then placed in tube-closing position, bringing the body 50 or 50a into contact with the nib, for transfer of the sample by absorption from the nib into the body 50 or 50a and thence into the strip 44 or column 46. Owing to the separation of the analysis element from the nib until sample collection has been completed, the quantity of the collected sample is definite, viz. determined by the saturation capacity of the nib alone, as desired for quantitative analytical purposes. In addition, after transfer of sample to the strip or web, the analysis element can be withdrawn from the tube 11 for further analytical procedures.

Conveniently, in embodiments such as those of FIGS. 8 and 11, and also in the embodiments shown in FIGS. 9 and 12 and described below, the device is provided with a separate cap (e.g. of the type illustrated as cap 16 in FIG. 1) to close the tube end 18, for preventing contamination prior to insertion of the analysis element and after the analysis element is removed, i.e. for sealing the tube at all times before, during and after sample collection except when the analysis element is in place. The analysis element and its cap 16' or 16" can be kept in a separate sealed container at those times when the tube is closed by the aforementioned separate cap.

In the modification shown in FIGS. 9 and 12, the body 50 or 50a of FIGS. 8 and 11 is replaced with a solid porous body 52 or 52a similarly disposed at the distal end of the analysis element for fluid-transmitting contact with (but, again, preferably separable from) the nib. The body 52 or 52a is not water-wettable; for example, it may be made of the same hydrophobic plastic as the nib (e.g. polyethylene or polypropylene) without the wetting agent used in the nib. Consequently, even if the cap 16' or 16" is in closed position and the body 52 or 52a is in contact with the nib, as shown, during collection of a body fluid sample by the nib, the sample cannot migrate beyond the nib to the strip 44 or column 46 because its ascent is blocked by the hydrophobic body 52 or 52a.

In a method of using the device of FIGS. 9 or 12 in accordance with the invention, sample collection by the nib is performed in the same manner as described above with reference to FIG. 4, with the body 52 or 52a at least optionally in contact with the nib 12 as illustrated. After sample collection is complete, the exposed tip of the nib is brought into contact with a nonaqueous solvent capable of absorption by the material of body 52 or 52a, e.g. a developing solvent which selectively transports a particular component or components of the initially collected sample from the nib through the body 52 or 52a and into the strip 44 or column 46. The embodiments of FIGS. 9 and 12 thus afford the advantages of the devices of FIGS. 8 and 11 with respect to determinability of sample volume and (where the body 52 or 52a is separable from the nib) subsequent removability of the sample-bearing analysis element for further testing. Furthermore, they permit performance of sample collection without removal or displacement of the cap 16' or 16", and they enable selective transport of particular sample components to the strip or column by use of an appropriate developing solvent with minimal manipulation of the device.

Figure 15:
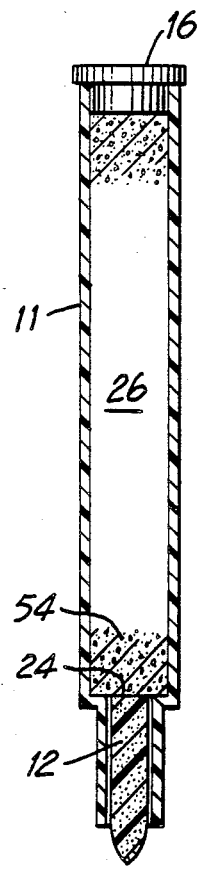
FIG. 15 is a view similar to FIG. 7 of another embodiment of the invention wherein the interior of the tube is entirely filled with a packed column of chromatographic powder.
Figure 16:
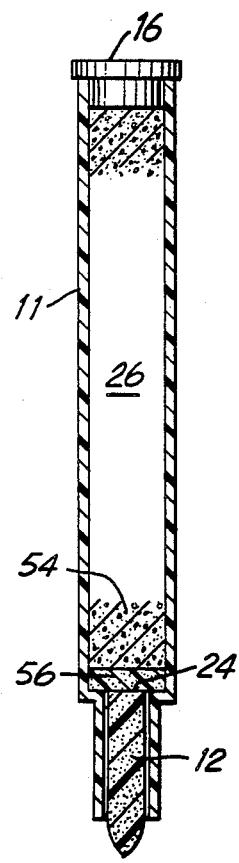
FIG. 16 is a like view of an embodiment of the invention differing from that of FIG. 15 in having a hydrophobic absorbent disc interposed between the nib and the packed column.

In the embodiments shown in FIGS. 15 and 16, a device having the structure of FIGS. 1 and 2 is provided with a packed column 54 of chromatographic powder or particles filling the entirety of the space 26 within the tube 11, and held therein by the cap 16. The column 54 in FIG. 15 is in direct fluid-transferring contact with the inner extremity 24 of the nib 12, as is suitable where retardation of sample transport into the column is unnecessary. In FIG. 16, the column 54 is isolated from the nib by a porous, absorbent, but hydrophobic disc-shaped body 56, e.g. fabricated of polyethylene or polypropylene without a wetting agent; this disc 56 serves the same purpose, and is used in the same way, as the bodies 52 and 52a of FIGS. 9 and 12, viz. to retard sample transfer to the column 54 during sample collection and to enable such transfer subsequently, for example, with the aid of a suitable nonaqueous developing solvent absorbed through the nib. In each of these embodiments of Figs. 15 and 16, the packed column 54 of chromatographic or other analytical powder undergoes some (e.g. visually or instrumentally observable) change upon contact, or subsequent development, with a substance to be detected, thereby to provide an analytical indication of the presence or absence of such substance in a collected sample.

While the described devices incorporating an analysis element have particular utility for nonintrusive sampling, they may also be employed in the collection and analysis of blood samples.

It is to be understood that the invention is not limited to the features and embodiments hereinabove set forth, but may be carried out in other ways without departure from its spirit.

I claim:

1. A device for nonintrusively collecting a sample of a fluid such as sweat, tears or saliva, comprising:
   (a) a hollow tube having at least one open end; and
   (b) a collecting nib secured in said one end of said tube and having an inner extremity facing the interior of the tube and an outer tip projecting beyond said one end of the tube for contact with a fluid to be collected, said nib comprising a solid, nonfibrous, porous, water-wettable body a porosity sufficient for absorption therein of the fluid to be collected, and said nib and said one end of said tube being mutually arranged to permit passage of fluid between the exterior and the interior of the tube at said one end only through the nib body.

2. A device as defined in claim 1, wherein said tube has a second open end opposed to said one open end.

3. A device as defined in claim 2, further including a cap for closing said second open end of the tube.

4. A device as defined in claim 3, further including a second cap for externally enclosing the nib and said one open end of said tube.

5. A device as defined in claim 1, wherein the nib body is fabricated of a material selected from the class consisting of polyethylene and polypropylene.

6. A device as defined in claim 1, wherein the nib body and the tube are bonded together by ultrasonic welding at said one end of the tube.

7. A device as defined in claim 1, wherein the nib body is press-fitted into said one end of the tube.

8. A device as defined in claim 1, wherein the nib body and the tube are joined by heat sealing.

9. A device as defined in claim 1, wherein said nib tip is substantially pointed.

10. A device as defined in claim 1, wherein said nib tip is substantially rounded.

11. A device as defined in claim 1, wherein said nib incorporates an agent capable of changing color on contact with a substance to be detected.

12. A device as defined in claim 1, wherein said tube is formed with an external annular ledge facing said one end to serve as a bearing surface for support of the tube in upright position with the nib oriented downwardly.

13. A device as defined in claim 1, wherein said tube has a second open end opposed to said one open end, and further including a cap for closing said second open end, and an elongated, absorbent, substantially rigid analysis element extending through the tube for fluid-transferring contact with the inner extremity of the nib to receive and absorb fluid collected by the nib; and wherein said analysis element has a proximal end mounted in said cap and a distal end disposed for contact with said nib inner extremity when said cap is in position closing said second open end.

14. A device as defined in claim 13, wherein said analysis element comprises a strip of web material having a distal end secured to said nib.

15. A device as defined in claim 13, wherein said analysis element comprises a strip of web material, and, mounted at the distal end thereof, a porous absorbent solid body disposed for fluid-transferring contact with the inner extremity of the nib.

16. A device as defined in claim 15, wherein said last-mentioned body is hydrophobic.

17. A device as defined in claim 13, wherein said analysis element comprises a packed column having a distal end secured to said nib.

18. A device as defined in claim 13, wherein said analysis element comprises a packed column and, mounted at the distal end thereof, a porous absorbent solid body disposed for fluid-transferring contact with the inner extremity of the nib.

19. A device as defined in claim 18, wherein said last-mentioned body is hydrophobic.

20. A device as defined in claim 13, wherein said analysis element incorporates an agent which undergoes an observable change upon contact with a substance to be detected, and wherein said tube is transparent.

21. A device as defined in claim 1, wherein said tube has a second open end opposed to said one open end, and further including a cap for closing said second open end, and a packed columm of particules filling said tube and in fluid-transferring contact with the inner extremity of said nib, said particules comprising an agent which undergoes an observable change upon contact with a substance to be detected.

22. A device as defined in claim 1, wherein said tube has a second open end opposed to said one open end, and further including a cap for closing said second open end, a porous absorbent hydrophobic solid body disposed within the tube in fluid-transferring contact with the inner extremity of the nib, and a packed column of particles filing said tube and in fluid-transmitting contact with said hydrophobic solid body, said particles comprising an agent which undergoes an observable change upon contact, or subsequent development, with a substance to be detected.

23. A device as defined in claim 1, wherein said tube is shaped and dimensioned for insertion in the human mouth with said tip positioned under the tongue for collection of a sample of saliva.

* * * * *